United States Patent [19]

Treiber et al.

[11] Patent Number: 5,371,088
[45] Date of Patent: Dec. 6, 1994

[54] 1-ARYL-4-PIPERAZINYLCYCLOHEX-ANECARBONITRILES, THE PREPARATION AND USE THEREOF

[75] Inventors: Hans-Joerg Treiber, Bruehl; Hans P. Hofmann, Limburgerhof; Laszlo Szabo, Dossenheim, all of Germany

[73] Assignee: BASF Aktiengesellschaft, Ludwigshafen, Germany

[21] Appl. No.: 117,103

[22] PCT Filed: Mar. 5, 1992

[86] PCT No.: PCT/EP92/00488

§ 371 Date: Sep. 14, 1993

§ 102(e) Date: Sep. 14, 1993

[87] PCT Pub. No.: WO92/16516

PCT Pub. Date: Oct. 1, 1992

[30] Foreign Application Priority Data

Mar. 15, 1991 [DE] Germany .............. 4108527

[51] Int. Cl.$^5$ .............. A61K 31/495; C07D 295/088; C07D 295/13; C07D 295/155
[52] U.S. Cl. .............. 514/252; 514/255; 544/360; 544/379; 544/398; 544/401; 544/402
[58] Field of Search .............. 544/360, 379, 398, 401, 544/402; 514/252, 255

[56] References Cited

U.S. PATENT DOCUMENTS

| | | | |
|---|---|---|---|
| 2,722,529 | 11/1955 | Fleming et al. | 544/393 |
| 3,759,974 | 9/1973 | Treiber et al. | 558/408 |
| 3,773,939 | 11/1973 | Janssen | 514/255 |
| 4,369,184 | 1/1983 | Stokbrockx et al. | 546/187 |
| 4,528,194 | 7/1985 | Masaki | 514/255 |
| 4,663,325 | 5/1987 | Ohtaka et al. | 514/255 |
| 4,835,155 | 5/1989 | Kogure et al. | 514/255 |
| 4,880,808 | 11/1989 | Van Daele et al. | 514/255 |
| 4,918,073 | 4/1990 | Rüger et al. | 514/255 |
| 5,071,851 | 12/1991 | Buschmann et al. | 544/401 |

FOREIGN PATENT DOCUMENTS

| | | |
|---|---|---|
| 0034415 | 8/1981 | European Pat. Off. . |
| 1795362 | 1/1972 | Germany . |
| 1452413 | 10/1976 | United Kingdom . |
| 1520931 | 8/1978 | United Kingdom . |

*Primary Examiner*—Emily Bernhardt
*Attorney, Agent, or Firm*—Keil & Weinkauf

[57] ABSTRACT

Compounds of the formula

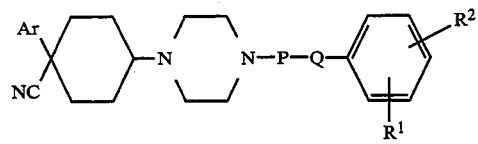

where Ar, $R^1$, $R^2$, P and Q have the meanings indicated in the description, and the preparation thereof are described. The compounds have antihypoxic and antiischemic action and are suitable for treating acute and chronic degenerative processes of the CNS and other organs.

4 Claims, No Drawings

1-ARYL-4-PIPERAZINYLCYCLOHEXANECAR-BONITRILES, THE PREPARATION AND USE THEREOF

The present invention relates to 1-aryl-4-piperazinylcyclohexanecarbonitriles, to processes for the preparation thereof and to the use thereof as drugs.

Derivatives of 4-amino-1-phenylcyclohexanecarbonitrile have been disclosed. Thus, ZA-C 66/5399 discloses compounds with morpholine- and mescalineantagonistic properties, and DE-B 17 93 383 discloses compounds with spasmolytic, hypotensive and neuroleptic properties. 4-Piperidinyl-1-phenylcyclohexanecarbonitriles with a strong antihistamine action have been described in EP-A 34 415.

In addition, a large number of substituted piperazines with antiarrhythmic or bloodflow-promoting properties has been disclosed. These are predominantly benzhydryl- or diarylbutylpiperazines, of which flunarizine is the best known compound. It is used for the therapy of disturbances of peripheral and cerebral blood flow (DE-A 19 29 330, DE-A 33 26 148, DE-A 25 47 570, EP-A 256 890, DE-A 36 00 390, EP-A 159 566, EP-A 285 219).

We have now found that 1-aryl-4-piperazinylcyclohexanecarbonitriles of the formula I

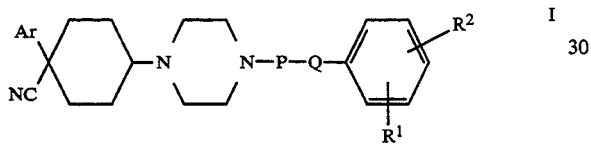

where
Ar is phenyl which is unsubstituted or monosubstituted by chlorine, methyl, methoxy or trifluoromethyl or mono- or disubstituted by fluorine, or is 2- or 3-thienyl or 2-, 3- or 4-pyridyl,
$R^1$ is hydrogen, fluorine, chlorine, trifluoromethyl, methoxy, methyl, nitro, cyano, acetyl, methoxycarbonyl or ethoxycarbonyl,
$R^2$ is hydrogen, chlorine or methyl,
P is straight-chain or branched alkylene of from 2 to 8 carbons, which can be monosubstituted by oxo, hydroxyl, methoxy or acetoxy, and
Q is oxygen or sulfur, NH or a bond,
and the salts thereof with physiologically tolerated acids, have an outstanding antihypoxic and antiischemic action.

Suitable physiologically tolerated acids are inorganic acids such as hydrochloric acid, sulfuric acid, phosphoric acid, nitric acid or organic acids such as tartaric acid, lactic acid, malic acid, citric acid, maleic acid, fumaric acid, oxalic acid, acetic acid, gluconic acid, mucic acid or methanesulfonic acid.

In formula I, Ar is preferably phenyl which is unsubstituted or monosubstituted by fluorine or chlorine, $R^1$ is preferably hydrogen, fluorine or chlorine or methoxy, and P-Q is, in particular, alkyleneoxy or alkylenethio of 2 or 3 carbons, or 2-hydroxypropyleneoxy. $R^1$ and $R^2$ can be in positions 2, 3 or 4 on the phenyl ring.

If P contains hydroxyl, for example, the compounds of the formula I have a center of chirality. They therefore exist in the form of optical antipodes (enantiomers). These can be obtained by conventional methods, by salt formation with chiral auxiliaries such as tartaric acid, dibenzoyltartaric acid or mandelic acid and fractional crystallization followed by liberation of the bases from the salts, or else by synthesis from suitable chiral precursors.

Furthermore, because of the cyclohexane ring, the compounds may also occur as cis and trans isomers. These geometrical isomers can be obtained in a conventional manner by separation processes such as crystallization or chromatography at the final stage or at an earlier stage, or else by carrying out suitable reactions.

The present invention also relates to processes for preparing the compounds of the formula I, which comprise either
a) reacting a compound of the formula II

where Ar has the stated meanings, with a piperazine derivative III

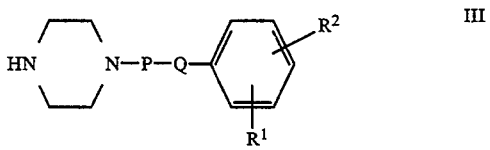

where P, Q, $R^1$ and $R^2$ have the stated meanings, or
b) reacting a compound of the formula IV

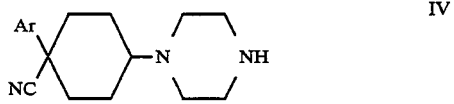

where Ar again has the abovementioned meanings, with a compound of the formula V

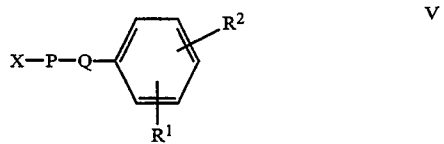

where P, R1 and R2 [sic] have the abovementioned meanings, and X is a reactive acid residue, or
c) if P is monosubstituted by hydroxyl, and Q is not NH, reacting a compound of the formula IV with a compound of the formula VI

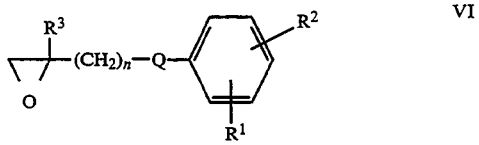

where Q, $R^1$ and $R^2$ have the abovementioned meanings, $R^3$ is $C_{1-4}$-alkyl, and n is 1 or 2,
and subsequently converting the resulting compounds where appropriate with physiologically tolerated acids into their salts.

The known reductive amination of compounds of the formula II with piperazines of the formula III can be carried-out with reducing agents such as catalytically activated hydrogen, in which case a noble metal catalyst such as palladium on carbon is preferably used, with complex metal hydrides such as sodium cyanoborohydride or else with formic acid in a suitable solvent at, preferably, from 0° to 100° C. Suitable solvents are acetonitrile, dimethylformamide, tetrahydrofuran, toluene or lower alcohols such as methanol or ethanol.

Depending on the reducing agent and the conditions used, either mixtures of the cis and trans isomers or the substantially pure, more stable cis isomer are obtained.

Process b) is preferably carried out in polar organic solvents such as alcohols (e.g. methanol, ethanol, isopropanol), a lower ketone (preferably acetone, methyl ethyl ketone or methyl isobutyl ketone), in dimethylformamide, dimethyl sulfoxide, acetonitrile or, where appropriate, also in a hydrocarbon such as toluene, advantageously in the presence of a base to trap the acid which is formed (such as sodium carbonate, potassium carbonate, calcium carbonate, triethylamine or pyridine) at elevated temperature, preferably at from 20° to 120° C. Suitable reactive acid residues X are chlorine, bromine or iodine atoms and sulfonate groups, preferably methanesulfonyl, benzenesulfonyl, p-toluenesulfonyl or trifluoromethanesulfonyl.

The conventional reaction of epoxides of the formula VI with the piperazines of the formula IV is expediently carried out in a solvent such as acetonitrile, dimethylformamide, tetrahydrofuran or a lower alcohol (preferably methanol or ethanol) at elevated temperatures (from 30° to 120° C.), preferably at boiling points [sic] of the solvent. If optically active epoxides are employed, the compounds according to the invention are obtained as pure enantiomers.

The starting compounds of the formulae II to VI are disclosed in the literature or can be prepared in a conventional manner.

The compounds according to the invention are suitable for treating acute and chronic degenerative processes of the central nervous system and other organs. These include, in particular, disorders attributable to an acute or chronic disturbance of the blood supply or of cellular metabolism, such as ischemic cerebral insults, cerebral hemorrhages, vascular encephalopathies and the dementias resulting therefrom, hypoglycemias, epilepsies, migraine, traumatic lesions of the brain and of the spinal cord, and ischemia-related degeneration of the heart, of the kidneys and of other organs, especially in connection with transplants and other surgical interventions.

The cerebroprotective action of the novel compounds was estimated on the normobaric hypoxic hypoxia of mice and on the global cerebral ischemia of mice (methods in: H. P. Hofmann et al., Arzneim.-Forsch./-Drug Res. 39, 1989, 304–308). The novel substances proved in both models to have pronounced protective activity, which was evident from the great increase in the survival time of substance-treated animals compared with placebo-treated control animals.

Likewise, the neuroprotective action of the novel substances was demonstrated in the model of temporary forebrain ischemia in the Mongolian gerbil (method in: L. Szabo and H. P. Hofmann, Arzneim.-Forsch./Drug Res.39, 1989, 314–319). In placebo-treated control animals, the brief interruption of the blood supply leads to the death of ischemia-sensitive nerve cells in the hippocampus. Treatment with the novel compounds distinctly reduces the extent of neuronal damage, which represents a relevant parameter for the antiischemic activity of the novel substances.

The compounds according to the invention can be administered orally, rectally or parenterally (subcutaneously, intravenously, intramuscularly, transdermally) in a conventional manner.

The dosage depends on the age, condition and weight of the patient and on the mode of administration. As a rule, the daily dose of active substance is from about 0.1 to 20 mg/kg of body weight on oral administration and from about 0.01 to 2 mg/kg of body weight on parenteral administration. Satisfactory results are normally achieved with daily oral doses of from 10 to 100 mg and parenteral doses of from 1 to 10 mg.

The novel compounds can be administered in the conventional solid or liquid pharmaceutical forms, e.g. uncoated or (film-)coated tablets, capsules, powders, granules, suppositories, solutions, ointments, creams, sprays or transdermal therapeutic systems. These are prepared in a conventional manner in which the active substances can be processed with the conventional pharmaceutical auxiliaries such as tablet binders, fillers, preservatives, tablet disintegrants, flow regulators antioxidants and/or propellant gases (cf. H. Sucker et al., Pharmazeutische Technologie, Thieme-Verlag, Stuttgart, 1978). The pharmaceutical forms obtained in this way normally contain from 1 to 75% by weight of the active substance.

EXAMPLES

A. Preparation of the Starting Compounds a)
4-(4-benzylpiperazinyl)1-phenylcyclohexanecarbonitrile 35.0 g of 4-cyano-4-phenylcyclohexanone (0.176 mol), (prepared as disclosed in J. Amer. Chem. Soc. 74, (1972) 773) were dissolved with 31 g of 1-benzylpiperazine (0.176 mol) and 21 g of acetic acid in 200 ml of ethanol and, at room temperature, a solution of 12.5 g of sodium cyanoborohydride (0.19 mol) was slowly added dropwise. The mixture was stirred overnight, and then water was added and the mixture was extracted with dichloromethane. Drying and removal of the solvent by distillation resulted in a residue of 46.6 g (76%) of oil.

The dihydrochloride was obtained by treatment with hydrochloric acid in isopropanol, $C_{24}H_{29}N_3 \times 2$ HCl, melting point <300° C.

Thin-layer chromatography and NMR of this product showed that it was composed of roughly equal amounts of the cis and trans isomers.

b)
cis-4-(4-benzylpiperazinyl)1-phenylcyclohexanecarbonitrile

The isomer mixture from a) was dissolved in ethyl acetate, and hexane was added to opalescence. The pure cis compound crystallized out overnight. Filtration with suction resulted in 15.5 g (33%).$C_{24}H_{29}N_3$, melting point 120°–123° C.

c)
cis-4-(4-benzylpiperazinyl)1-phenylcyclohexanecarbonitrile 5 g of 4-cyano-4-phenylcyclohexanone (0.025 mol) were heated with 4.4 g (0.025 mol) of 1-benzylpiperazine to 100° C. and then 1.5 ml of formic acid were slowly added dropwise while stirring, and the mixture was stirred at 100° C. for a further 3 h. After cooling, 10 ml of ethyl acetate/hexane mixture were added: after leaving to stand overnight, 5.0 g (55%) of pure compound were obtained. $C_{24}H_{29}N_3$, melting point 120°–123° C.

d) 4-piperazinyl- 1-phenylcyclohexanecarbonitrile 12.7 g (0.035 mol) of the product prepared as in a) were hydrogenated with 1 g of 10% Pd on carbon catalyst and hydrogen in methanolic hydrochloric acid solution under atmospheric pressure. After hydrogen uptake ceased, the catalyst was filtered off and the solution was evaporated. After treatment with alkali and extraction with ether, the above base was isolated as cis/trans isomer mixture.

$C_{17}H_{23}N_3$, yield 95%, $C_{17}H_{23}N_3 \times 2$ HCl dihydrochloride, melting point >330° C.

e) cis-4-piperazinyl-1-phenylcyclohexanecarbonitrile

The compound was obtained from the product obtained as in b) by hydrogenation in a similar manner to d). Yield $C_{17}H_{23}N_3$, melting point 109°–113° C.

B) Preparation of the Compounds According to the Invention

Process a.

EXAMPLE 1 cis-(4-Cinnamyl)piperazinyl-1-phenylcyclohexanecarbonitrile 6.0 g (0.03 mol of 4-cyano-4-phenylcyclohexanone were heated with 6.1 g (0.03 mol) of cinnamylpiperazine to 100° C. and then 1.5.g (0.033 mol) of formic acid were slowly added dropwise, while stirring, and the mixture was stirred at 100° C. for a further 3 h. It was then diluted with ethyl acetate and washed with 2N sodium hydroxide solution. The organic phase was dried and evaporated. The residue was taken up in isopropanol and the hydrochloride was obtained by addition of isopropanolic hydrochloric acid. Yield: 50% $C_{26}H_{31}N_3 \times 2$ HCl dihydrochloride, melting point >250° C.

The following were prepared in a similar manner:

EXAMPLE 2 cis-4-{4-[3-(4-Fluorophenoxy)-2-hydroxypropyl]-piperazinyl}1-(4-fluorophenyl)cyclohexanecarbonitrile $C_{26}H_{41}F_2N_3 \times 2$ HCl dihydrochloride, melting point >250° C.

EXAMPLE 3 cis-4-{4-[3-(4-Fluorophenoxy)-2-hydroxypropyl]-piperazinyl}1-(2-chlorophenyl)cyclohexanecarbonitrile $C_{26}H_{31}ClFN_3O_2 \times 2$ HCl dihydrochloride, melting point >250° C.

EXAMPLE 4 cis-4-{4-[3-Phenoxy-2-hydroxypropyl]piperazinyl}1-(3methoxyphenyl)cyclohexanecarbonitrile $C_{27}H_{35}N_3O_3 \times 2$ HCl dihydrochloride, melting point >290° C.

EXAMPLE 5 cis-4-[4-(3-Phenoxy-2-hydroxypropyl)piperazinyl}1-phenylcyclohexanecarbonitrile $C_{26}H_{33}N_3O_2 \times 2$ HCl dihydrochloride, melting point >250° C.

EXAMPLE 6 cis-4-{4-[3-(4-Fluorophenoxy)-2-hydroxypropyl]-piperazinyl}1-(2-pyridyl)cyclohexanecarbonitrile $C_{25}H_{31}FN_4O_2 \times 2$ HCl dihydrochloride, melting point 274°–278° C.

EXAMPLE 7 cis-4-{4-[2-(4-Fluorophenoxy)ethyl]piperazinyl}1-(2-pyridyl)cyclohexanecarbonitrile $C_{24}H_{29}FN_4O \times 2$ HCl dihydrochloride, melting point 282°–287° C.

EXAMPLE 8 cis-4-{4-[3-(4-Fluorophenoxy)-2-hydroxypropyl]-piperazinyl}1-(2-thienyl)cyclohexanecarbonitrile $C_{24}H_{30}FN_3O_2S \times 2$ HCl dihydrochloride, melting point >250° C.

EXAMPLE 9 cis-4-{4-[2-(4-Fluorophenoxy)ethyl]piperazinyl}1-(4-chlorophenyl)cyclohexanecarbonitrile $C_{25}H_{29}ClFN_3O \times 2$ HCl dihydrochloride, melting point 270°–280° C.

EXAMPLE 10 cis-4-{4-[3-(4-Fluorophenoxy)-2-hydroxypropyl]-piperazinyl}1-(3-methoxyphenyl)cyclohexanecarbonitrile $C_{27}H_{34}FN_3O_3 \times 2$ HCl dihydrochloride, melting point 290°–300° C.

EXAMPLE 11 cis-4-{4-[3-(4-Fluorophenoxy)-2-hydroxypropyl]-piperazinyl}1-(3-chlorophenyl)cyclohexanecarbonitrile $C_{26}H_{31}ClFN_3O_2 \times 2$ HCl dihydrochloride, melting point >250° C.

EXAMPLE 12 cis-4-{4-[3-(4-Fluorophenoxy)-2-hydroxypropyl]-piperazinyl}1-(4-methoxyphenyl)cyclohexanecarbonitrile $C_{27}H_{34}FN_3O_3 \times 2$ HCl dihydrochloride, melting point >280° C.

EXAMPLE 13 cis-4-{4-[3-(4-Fluorophenoxy)-2-hydroxypropyl]-piperazinyl}1-(2-methoxyphenyl)cyclohexanecarbonitrile $C_{27}H_{34}FN_3O_3 \times 2$ HCl dihydrochloride, melting point >250° C.

EXAMPLE 14 cis-4-{4-[3-(4-Fluorophenoxy)-2-hydroxypropyl]-piperazinyl}1-(4-hydroxyphenyl)cyclohexanecarbonitrile $C_{26}H_{32}FN_3O_3 \times 2$ HCl dihydrochloride, melting point >250° C.

EXAMPLE 15

4-[4-(3-Phenoxypropyl)piperazinyl-1-phenylcyclohexanecarbonitrile [sic]

5.0 g (0.025 mol) of 4-cyano-4-phenylcyclohexanone and 5.5 g (0.025 mol) of 3-phenoxypropylpiperazine were dissolved with 3.0 g of acetic acid in 70 ml of ethanol and then, while stirring at room temperature, a solution of 1.7 g (0.027 mol) of sodium cyanoborohydride was slowly added dropwise. The mixture was stirred overnight and then diluted with water and extracted with dichloromethane. The organic phase was subsequently washed with dilute acid (pH 4), dilute sodium hydroxide solution and water and finally dried and evaporated. The residue was converted into the hydrochloride with isopropanolic hydrochloric acid, and the product was recrystallized from isopropanol/water. Yield: 50%, $C_{26}H_{33}N_3O \times 2$ HCl dihydrochloride, melting point >250° C.

The following compounds were prepared in a similar manner:

EXAMPLE 16

4-{4-[3-(4-Fluorophenoxy)-2-hydroxypropyl]piperazinyl}1-(2-methylphenyl)cyclohexanecarbonitrile $C_{27}H_{34}FN_3O_2 \times 2$ HCl dihydrochloride, melting point >250° C.

EXAMPLE 17

4-{4-[2-(4-Chlorothiophenoxy)ethyl]piperazinyl}1-phenylcyclohexanecarbonitrile [sic]

$C_{25}H_{30}ClN_3S \times 2$ HCl dihydrochloride, melting point >270° C.

EXAMPLE 18

4-{4-[3-(4-Fluorophenoxy)propyl]piperazinyl}1-phenylcyclohexanecarbonitrile $C_{26}H_{32}FN_3O \times 2$ HCl dihydrochloride, melting point >250° C.

The cis/trans isomers of the compound were separated by preparative column chromatography.
Sorbent: silica gel
Eluent: dichloromethane with 1.5% methanol
Thin-layer chromatography: silica gel plates
Mobile phase: dichloromethane/methanol 90:10
Migration distance: 10 cm
Visualization method: $I_2$ vapor
The following were obtained:

EXAMPLE 19 cis-4-{4-[3-(4-Fluorophenoxy)propyl]piperazinyl}1-phenylcyclohexanecarbonitrile $C_{26}H_{32}FN_3O \times 2$ HCl dihydrochloride, melting point >250° C. Rf=0.17.

EXAMPLE 20 trans-4-{4-[3-(4-Fluorophenoxy)propyl]piperazinyl}1-phenylcyclohexanecarbonitrile $C_{26}H_{32}FN_3O \times 2$ HCl dihydrochloride, melting point >250° C., Rf=0.23 [methylene chloride/methanol] 9:1, silica gel [sic].
Process b.

EXAMPLE 21 cis-4-{4-[2-(4-Chlorophenoxy)ethyl]piperazinyl}1-phenylcyclohexanecarbonitrile 5.4 g (0.02 mol) of the piperazine from f, 4.7 g (0.02 mol) of 2-(4-chlorophenoxy)ethyl bromide and 5.5 g of calcium carbonate in 100 ml of methyl ethyl ketone were refluxed for 4 h. The salts were removed and then the filtrate was evaporated, the residue was taken up in dichloromethane, and the solution was washed with water, dried and evaporated under reduced pressure. The substance was dissolved in isopropanol and converted into the hydrochloride by addition of isopropanolic hydrochloric acid. Yield: 60%, $C_{25}H_{30}ClN_3O \times 2$ HCl dihydrochloride, melting point >250° C.

The following were obtained in a similar manner:

EXAMPLE 22 cis-4-{4-[2-(4-Fluorophenoxy)ethyl]piperazinyl}1-phenylcyclohexanecarbonitrile $C_{25}H_{30}FN_3O \times 2$ HCl dihydrochloride, melting point >260° C.,

EXAMPLE 23 cis-4-{4-[2-(4-Fluorophenoxy)ethyl]piperazinyl}1-(4-fluorophenyl)cyclohexanecarbonitrile $C_{25}H_{29}F_2N_3O \times 2$ HCl dihydrochloride, melting point >260° C.,

EXAMPLE 24 cis-4-{4-[(4-Chlorophenoxy)acetyl]piperazxinyl}1-phenylcyclohexanecarbonitrile $C_{25}H_{28}ClN_3O_2$, melting point 165°–170° C.,

EXAMPLE 25 cis-4-{4-[(N-Phenylcarboxamido)methyl]piperazinyl}-1-phenylcyclohexanecarbonitrile [sic]

$C_{25}H_{30}N_4O \times 2$ HCl dihydrochloride, melting point >300° C.,

EXAMPLE 26 cis-4-{4-[(N-(2,6-Dimethylphenyl)carboxamido)methyl]piperazinyl}-1-phenylcyclohexanecarbonitrile [sic]

$C_{27}H_{34}N_4O \times 2$ HCl dihydrochloride, melting point 295°–300° C.,

EXAMPLE 27 cis-4-{4-[3-Phenoxypropyl]piperazinyl}-1-phenylcyclohexanecarbonitrile $C_{26}H_{33}N_3O \times 2$ HCl dihydrochloride, melting point >250° C.,
Process c.

EXAMPLE 28 cis-4-{4-[4-Fluorophenoxy]-2-hydroxybutyl]piperazinyl } -1-phenylcyclohexanecarbonitrile 3.7 g (0.0147 mol) of the piperazine prepared as in Example A.e) and 2.5 g (0.0147 mol) of 1,2-epoxy-4(4-fluorophenoxy)butane were dissolved in 70 ml of ethanol and refluxed for 4 h. After the reaction was complete, isopropanolic hydrochloric acid was added to the mixture and the resulting hydrochloride was recrystallized from an isopropanol/water mixture. Yield: 70%

$C_{27}H_{34}FN_3O_2 \times 2$ HCl dihydrochloride, melting point >250° C.

The following compounds were obtained in a similar manner starting from the piperazine obtained as in A.e) by reaction with various substituted 1,2-epoxy-3-phenoxypropanes:

EXAMPLE 29 cis-4-{4-[3-Phenoxy-2-hydroxypropyl]piperazinyl}-1-phenylcyclohexanecarbonitrile $C_{26}H_{33}N_3O_2 \times 2$ HCl dihydrochloride, melting point >250° C.,

EXAMPLE 30 cis-4-{4-[3-(Phenylmercapto)-2-hydroxypropyl]-piperazinyl}-1-phenylcyclohexanecarbonitrile $C_{26}H_{33}N_3OS \times 2$ HCl dihydrochloride, melting point >250° C.,

EXAMPLE 31 cis-4-{4-[3-Chlorophenoxy)-2-hydroxy]propyl}piperazinyl}-1-phenylcyclohexanecarbonitrile [sic]

$C_{26}H_{32}ClN_3O_2 \times 2$ HCl dihydrochloride, melting point >250° C.,

EXAMPLE 32 cis-4-{4-[3-(2-Cyanophenoxy)-2-hydroxypropyl]-piperazinyl}-1-phenylcyclohexanecarbonitrile $C_{27}H_{32}N_4O_2 \times 2$ HCl dihydrochloride, melting point >250° C.,

EXAMPLE 33 cis-4-{4-[3-(4-Nitrophenoxy)-2-hydroxypropyl]-piperazinyl}-1-phenylcyclohexanecarbonitrile $C_{26}H_{32}N_4O_4 \times 2$ HCl dihydrochloride, melting point >250° C.,

EXAMPLE 34 cis-4-{4-[3-(3-Trifluoromethylphenoxy)-2-hydroxypropyl]piperazinyl}-1-phenylcyclohexanecarbonitrile $C_{27}H_{32}F_3N_3O_2 \times 2$ HCl dihydrochloride, melting point >250° C.,

EXAMPLE 35 cis-4-{4-[3-(2-Methoxyphenoxy)-2-hydroxypropyl]-piperazinyl}-1-phenylcyclohexanecarbonitrile $C_{27}H_{35}N_3O_3 \times 2$ HCl dihydrochloride, melting point >250° C., The following was obtained using 1,2-epoxy-3-phenylpropane:

EXAMPLE 36 cis-4-{4-[3-Phenyl-2-hydroxypropyl]piperazinyl}-1-phenylcyclohexanecarbonitrile $C_{26}H_{33}N_3O \times 2$ HCl dihydrochloride, melting point >250° C., The following was obtained in a similar manner by reacting the piperazine from Example e) with. p-chlorostyrene oxide:

EXAMPLE 37 cis-4-{4-[2-(4-Chlorophenyl)-2-hydroxyethyl]-piperazinyl}-1-phenylcyclohexanecarbonitrile $C_{25}H_{30}ClN_3O \times 2$ HCl dihydrochloride, melting point >250° C.,

EXAMPLE 38 cis-4-{4-[2-(4-Fluorophenyl)-2-hydroxyethyl]-piperazinyl}-1-phenylcyclohexanecarbonitrile $C_{28}H_{30}FN_3O \times 2$ HCl dihydrochloride, melting point >300° C.,

EXAMPLE 39 cis-4-{4-[3,3-Dimethyl-3-phenyl-2-hydroxypropyl]-piperazinyl}-1-phenylcyclohexanecarbonitrile $C_{28}H_{37}N_3O \times 2$ HCl dihydrochloride, melting point >300° C.,

EXAMPLE 40 cis-4-{4-[3-(4-Chlorophenoxy)-2-t-butyl-2-hydroxypropyl]piperazinyl}-1-phenylcyclohexanecarbonitrile $C_{30}H_{40}ClN_3O_2 \times 2$ HCl dihydrochloride, melting point >285°–290° C.,

EXAMPLE 41 cis-4-{4-[3-Phenoxy-2-hydroxy-2-methyl]piperazinyl}-1-phenylcyclohexanecarbonitrile [sic]

$C_{27}H_{35}N_3O_2 \times 2$ HCl dihydrochloride, melting point >270° C.,

EXAMPLE 42 cis-4-{4-[3-(2,4-Dichlorophenoxy-2-hydroxy-2-methylpropyl] piperazinyl}-1-phenylcyclohexanecarbonitrile $C_{27}H_{33}Cl_2N_3O_2 \times 2$ HCl dihydrochloride, melting point >270° C.,

EXAMPLE 43 cis-4-{4-[3-(4-Acetylphenoxy)-2-hydroxypropyl]piperazinyl}-1-phenylcyclohexanecarbonitrile $C_{28}H_{35}N_3O_3 \times 2$ HCl dihydrochloride, melting point >280° C.,

EXAMPLE 44 cis-4-{4-[3-(2-Carbomethoxy)-phenoxy-2-hydroxypropyl]piperazinyl}-1-phenylcyclohexanecarbonitrile [sic]

$C_{28}H_{35}N_3O_4 \times 2$ HCl dihydrochloride, melting point 250°–260° C.

Reaction of the cis/trans mixture, obtained as in A.d), of the piperazine with (+)-1,2-epoxy-3,-(4-fluorophenoxy)propane as in Example 28 resulted in cis/trans isomers which were separated by preparative column chromatography as described in Example 18.

The following were isolated:

EXAMPLE 45

(−)trans-4-{4-[3-(4-Fluorophenoxy)-(S)-2-hydroxypropyl]piperazinyl}-1-phenylcyclohexanecarbonitrile $C_{26}H_{32}FN_3O_2 \times 2$ HCl dihydrochloride, melting point >250° C., $[\alpha]^{20}_{589\ nm}$ [sic]= −12.1° (C=10 mg/ml, methanol 95%) Rf=0.4

EXAMPLE 46

(−)cis-4-{4-[3-(4-Fluorophenoxy)-(S)-2-hydroxypropyl]piperazinyl}-1-phenylcyclohexanecarbonitrile a) $C_{26}H_{32}FN_3O_2 \times 2$ HCl dihydrochloride, melting point >250° C., b) $C_{26}H_{32}FN_3O_2 \times 2$ $CH_3SO_3H$ bismethanesulfonate, melting point >250° C., c) $C_{26}H_{32}FN_3O_2$ base, melting point >250° C., $[\alpha]^{20}_{589\,nm}$ [sic] = −10.1° (C=10 mg/ml, methanol 95%) Rf=0.3

The following were obtained by similar reaction with (−)-1,2-epoxy-3-(4-fluorophenoxy)propane followed by chromatography:

EXAMPLE 47

(+)-trans-4-{4-[3-(4-Fluorophenoxy)-(R)-2-hydroxypropyl]-piperaziny}-1-phenylcyclohexanecarbonitrile [sic]

$C_{26}H_{32}FN_3O_2 \times 2$ HCl dihydrochloride, melting point >250° C., $[\alpha]^{20}_{589\,nm}$ [sic] = −11.1° (C=10 mg/ml, methanol 95%) Rf=0.4

EXAMPLE 48

(+)-cis-4-{4-[3-(4-Fluorophenoxy)-(R)-2-hydroxypropyl]piperaziny}-1-phenylcyclohexanecarbonitrile [sic]

$C_{26}H_{32}FN_3O_2 \times 2$ HCl dihydrochloride, melting point >250° C. $C_{26}H_{32}FN_3O_2$ base, melting point 143°–149° C. $[\alpha]^{20}_{589\,nm}$ [sic] = 9.6° (C=10 mg/ml, methanol 95%)

When the reaction was carried out with pure trans-piperazine from Example A.e) and (+)- or (−)-1,2-epoxy-3-(4-fluorophenoxy)propane, the substances of Examples 46 and 48 were obtained in a yield of 70%.

EXAMPLE 49 cis-(−)-4-{4-[3-(4-Fluorophenoxy)-2-acetoxypropyl]-piperaziny}-1-phenylcyclohexanecarbonitrile [sic]

3 g of the base from Example 29 were refluxed with 30 ml of acetic anhydride for 1.5 h and then the excess acetic anhydride was removed by distillation under reduced pressure. The residue was dissolved in diisopropyl ether, and the substance was obtained as the dihydrochloride with ethereal hydrochloric acid.

$C_{28}H_{34}FN_3O_2 \times 2$ HCl dihydrocloride, melting point 272°–275° C.

EXAMPLE 50 cis-(−)-4-{4-[3-(4-Fluorophenoxy)-2-methoxypropyl]-piperazinyl}-1-phenylcyclohexanecarbonitrile 4.4 g (0.01 mol) of the base from Example 29 were stirred with 0.3 g of 80% sodium hydride 50 ml in DMF and 1.4 g (0.01 mol) of methyl iodide at 25°–40° C. for 12 h. After the reaction was complete, the mixture was diluted with 250 ml of water, the base was extracted with methylene chloride, the solution was dried, the solvent was removed by distillation, and the residue was converted with isopropanolic hydrochloric acid into the dihydrochloride:

$C_{27}H_{34}FN_3O_2 \times 2$ HCl dihydrochloride, melting point 270°–280° C.

We claim:

1. A 1-aryl-4-piperazinylcyclohexanecarbonitrile of the formula I

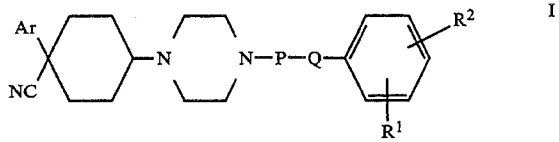

where

Ar is phenyl which is unsubstituted or monosubstituted by chlorine, methyl, methoxy or trifluoromethyl or mono- or disubstituted by fluorine, or is 2- or 3-thienyl or 2-, 3- or 4-pyridyl, $R^1$ is hydrogen, fluorine, chlorine, trifluoromethyl, methoxy, methyl, nitro, cyano, acetyl, methoxycarbonyl or ethoxycarbonyl, $R^2$ is hydrogen, chlorine or methyl, P is straight-chain or branched alkylene of from 2 to 8 carbons, which can be monosubstituted by oxo, hydroxyl, methoxy or acetoxy, and Q is oxygen or sulfur, NH or a bond, or the salts thereof with physiologically tolerated acids.

2. (−)-cis-4-{4-[3-(4-Fluorophenoxy)-(S)-2-hydroxypropyl]piperazinyl}-1-phenylcyclohexanecarbonitrile.

3. (−)-trans-4-{4-[3-(4-Fluorophenoxy)-(S)-2-hydroxypropyl]piperazinyl}-1-phenylcyclohexanecarbonitrile.

4. A method for control of diseases associated with hypoxia and ischemia which comprises administering to a patient in need thereof an antihypoxic or antiischemic effective amount of the 1-aryl-4-piperazinylcyclohexanecarbonitrile of formula I as set forth in claim 1.

* * * * *